United States Patent [19]

Kämmerer et al.

[11] 4,284,786
[45] Aug. 18, 1981

[54] 5-METHYLISOXAZOLE-4-CARBOXYLIC-(4-TRIFLUOROMETHYL)-ANILIDE

[75] Inventors: Friedrich-Johannes Kämmerer, Hochheim am Main; Rudolf Schleyerbach, Hofheim am Taunus, both of Fed. Rep. of Germany

[73] Assignee: Hoechst Aktiengesellschaft, Frankfurt am Main, Fed. Rep. of Germany

[21] Appl. No.: 103,551

[22] Filed: Dec. 13, 1979

[30] Foreign Application Priority Data

Dec. 16, 1978 [DE] Fed. Rep. of Germany ....... 2854439

[51] Int. Cl.³ .................... C07D 261/12; A61K 31/42
[52] U.S. Cl. ..................................... 548/248; 424/272
[58] Field of Search .......................................... 548/248

[56] References Cited

U.S. PATENT DOCUMENTS 4,087,535  5/1978  Heubach .............................. 548/248

FOREIGN PATENT DOCUMENTS 2524959  12/1979  Fed. Rep. of Germany ........... 548/248

*Primary Examiner*—Anton H. Sutto
*Attorney, Agent, or Firm*—Curtis, Morris & Safford

[57] ABSTRACT

5-Methylisoxazole-4-carboxylic acid-(4-trifluoromethyl)-anilide and a process for its preparation is described. The compound has an antirheumatic, antiphlogistic, antipyretic and analgesic action, and can be used for the treatment of multiple sclerosis.

1 Claim, No Drawings

5-METHYLISOXAZOLE-4-CARBOXYLIC-(4-TRI-FLUOROMETHYL)-ANILIDE

United Kingdom Patent Specification No. 1,547,452 discloses 5-methylisoxazole-4-carboxylic acid anilides having antiphlogistic and analgesic actions. On investigating similar compounds, it has now been found that if a trifluoromethyl group is introduced into the 4-position of the anilide moiety, a compound is obtained which is distinctly superior to the known 5-methylisoxazole-4-carboxylic acid anilides both in respect to its activity and therapeutic range, and also in respect to its pattern of action.

The invention relates to 5-methylisoxazole-4-carboxylic acid 4-trifluoromethyl-anilide of the formula I

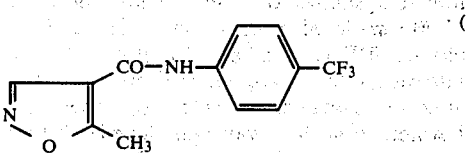

The invention further relates to a process for the preparation of the compound of the formula I, wherein 4-trifluoromethylaniline of the formula II

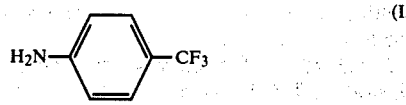

(a) is reacted with a 4-methylisoxazole-4-carboxylic acid derivative of the formula III

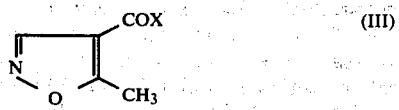

where X is either a halogen atom, preferably chlorine or bromine, or a YO— or Z0—CO—O—group, Y is phenyl which is optionally monosubstituted, disubstituted or trisubstituted by fluorine, chlorine, bromine, iodine, methyl, ethyl, methoxy, ethoxy, trifluoromethyl, nitro or cyano or is the acyl radical corresponding to formula III (namely formula III without X) and Z is ($C_1$—$C_4$)-alkyl, phenyl or benzyl, or (b) is reacted with diketene or a reactive acetoacetic acid derivative, the resulting acetoacetic acid anilide of the formula IV

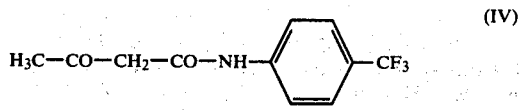

is heated with an orthoformic acid ester of the formula V

wherein R is ($C_1$-$C_4$)-alkyl and with an acid anhydride, and the resulting 2-alkoxymethylene-acetoacetic acid anilide of the formula VI

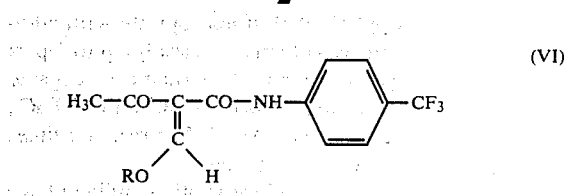

wherein R has the above meanings, is reacted with hydroxylamine.

The reaction according to process variant (a) is advantageously carried out in a dispersing medium or solvent which is inert towards the reactants under the reaction conditions. Examples of suitable media are nitriles, such as acetonitrile, ethers, such as diethyl ether, tetrahydrofuran, or dioxane, and alcohols, such as methanol, ethanol, propanol or isopropanol, as well as water.

In a preferred embodiment of process variant (a), trifluoromethylaniline of the formula II is reacted with the carboxylic acid chloride of the formula III, advantageously in the presence of an acid-binding agent, eg. potassium carbonate or sodium carbonate, an alkali metal hydroxide or alkaline earth metal hydroxide, an alkali metal alcoholate or alkaline earth metal alcoholate, or an organic base, such as triethylamine, pyridine, picoline or quinoline or the aniline of the formula II, used in excess, at temperatures between 0° and 160° C., preferably between 20° and 80° C. The reaction times can be from a few minutes up to two hours.

The 5-methylisoxazole-4-carboxylic acid derivatives of the formula III required as starting materials are obtained analogously to German Pat. No. 634,286 by reacting ethoxymethylene-acetoacetic acid ester with hydroxylamine to give the 5-methylisoxazole-4-carboxylic acid ester, hydrolyzing this ester under acid conditions, for example in a mixture of glacial acetic acid and concentrated hydrochloric acid in the ratio of 2:1, to give 5-methylisoxazole-4-carboxylic acid, and converting this carboxylic acid in accordance with customary methods to the carboxylic acid halides, esters or anhydrides.

To carry out process variant (b), 4-trifluoromethylaniline of the formula II is reacted with an advantageously at least equimolar amount of diketene or of a reactive acetoacetic acid derivative, for example a ($C_1$-$C_4$)-alkyl or aryl acetoacetate, preferably methyl, ethyl, phenyl or 2,4-dichlorophenyl acetoacetate, or an acetoacetic acid halide, advantageously in a solvent or dispersing medium which is inert towards the reactants under the reaction conditions, for example a nitrile, such as acetonitrile or an ether, such as diethyl ether, tetrahydrofuran or dioxane, at temperatures between 20° and 100° C., preferably between 40° and 80° C., and for reaction times of 10 minutes to 3 hours, the resulting acetoacetic acid anilide of the formula IV is warmed with an advantageously at least equimolar amount of an orthoformic acid ester of the formula V, advantageously in a 2-fold to 4-fold molar excess of an acid anhydride, suitably an aliphatic acid anhydride with 4 to 6 C atoms, preferably acetic anhydride, for 30 minutes to 3 hours, to a temperature between 80° and 150° C., preferably to the boiling point of the mixture, and the resulting 2-alkoxymethylene-acetoacetic acid anilide of the formula VI is isolated and subsequently reacted with an advantageously at least equimolar amount of hydroxylamine in an organic solvent or solvent mixture, preferably methyl alcohol, ethyl alcohol, propyl alcohol or isopropyl alcohol, if appropriate with addition of up to 2 parts by volume, preferably up to 1 part by volume, of water per part by volume of organic solvent, at a temperature of between 0° and 130° C., preferably between 20° and 100° C. The reaction times range from a few minutes to 5 hours.

The acetoacetic acid 4-trifluoromethyl-anilide of the formula IV, used as an intermediate product for carrying out process variant (b), and the 2-alkoxymethylene-acetoacetic acid anilides of the formula VI are new. They have an analgesic and antipyretic action and are therefore useful as medicaments.

After an optional filtration to remove by-products and concentration of the filtrate, the product of Formula I precipitates from the reaction mixture in the form of crystals, when the operations are carried out with the use of organic solvents. The product is obtained from an aqueous reaction mixture by extraction with a polar organic solvent such as methylene chloride, chloroform or trichloroethane, and concentration or evaporation of the extract. Subsequently, the product may be purified by recrystallization, for which an organic, preferably moderately polar solvent such as toluene, a dimethylbenzene, benzene, cyclohexane, methanol or ethanol, or a mixture of such solvents is employed.

By virtue of its pharmacological properties, the isoxazole compound according to the invention, of the formula I, can be used especially as an antirheumatic, antiphlogistic, antipyretic and analgesic agent, and for the treatment of multiple sclerosis. The compound can be administered either by itself, if appropriate in the form of micro-capsules, or in pharmaceutical compositions where it is mixed with suitable excipients. Accordingly, the invention also relates to pharmaceutical compositions consisting of the compound of formula I as the active ingredient, in addition to a customary physiologically and pharmaceutically acceptable excipient and/or diluent. The compositions can be administered orally, rectally or parenterally, oral or rectal use being preferred. Examples of suitable solid or liquid galenical formulations are granules, powders, tablets, capsules, suppositories, syrups, suspensions or drops, as well as preparations with protracted release of the active substance. Examples of commonly used excipients which may be mentioned are calcium carbonate, calcium phosphates, various sugars as lactose or tpyes of starch, cellulose derivatives, gelatin, vegetable oils, polyethylene glycols and other physiologically compatible solvents.

Pharmaceutical compositions according to the invention contain the compound of formula I for oral application, e.g. in the form of capsules, in a dose of from 25 to 150 milligrams, preferably 50–100 mg, and for rectal application, e.g. in the form of suppositories, in a dose of from 50–300, preferably 100–200 mg. Such compositions are applied one to four times per day according to the extent of the ailment, in most cases two to three times per day.

A further use of the compound of the formula I is to combine it with other suitable active substances, for example anti-uricopathic agents, thrombocyte aggregation inhibitors, other analgesic and other steroid or non-steroid antiphlogistic agents.

Examples of the preparation of
5-methylisoxazole-4-carboxylic cid
4-trifluoromethyl-anilide of the formula I Process variant (a)

1. A solution of 0.05 mole of 5-methylisoxazole-4-carboxylic acid chloride (III) (7.3 g) in 20 ml of acetonitrile is added dropwise, while stirring, to 0.1 mole of 4-trifluoromethylaniline (II) (16.1 g), dissolved in 150 ml of acetonitrile, at room temperature. After stirring for a further 20 minutes, the precipitated 4-trifluoromethylaniline hydrochloride is filtered off and washed with two 20 ml portions of acetonitrile, and the combined filtrates are concentrated under reduced pressure. 12.8 g (94.8% of theory) of white crystalline 5-methylisoxazole-4-carboxylic acid 4-trifluoromethyl-anilide of the formula I are thus obtained; melting point (after recrystallization from toluene) 166.5° C.

2. 0.1 mole of 5-methylisoxazole-4-carboxylic acid chloride (III) (14.6 g) and 20 ml of a 5 N potassium hydroxide solution are added dropwise to 0.1 mole of trifluoromethylaniline (II) (16.1 g), suspended in 150 ml of water, in such a way that the pH of the reaction mixture does not rise above 5. The mixture is subsequently shaken with 150 ml of methylene chloride. The methylene chloride phase is washed with water and, after drying with sodium sulfate is, evaporated to dryness under reduced pressure. This gives 24.4 g (90.2% of theory) of a crystalline product of the formula I, melting point (after recrystallization from toluene) 166.5° C.

3. 0.1 mole of 5-methylisoxazole-4-carboxylic acid chloride (III) (14.6 g), dissolved in 20 ml of acetonitrile, is added dropwise, with stirring, to a solution of 0.1 mole of 4-trifluoromethylaniline (II) (16.1 g) and 0.1 mole of triethylamine (5.06 g) in 300 ml of acetonitrile. The mixture is then stirred for a further 20 minutes. The by-products which have precipitated are filtered off. The filtrate is evaporated to dryness under reduced pressure. The residue is extracted by shaking with 300 ml of methylene chloride and 300 ml of water. The methylene chloride phase is washed with water, dried and evaporated to dryness under reduced pressure. This gives 21.1 g (78.1% of theory) of crystalline product of the formula I, melting point (after recrystallization from toluene) 166.5° C.

4. 0.1 mol of 4-trifluromethylaniline (II) (16.1 g) is refluxed for 1 hour with 0.1 mol of ethoxycarbonyl-5-methylisoxazole-4-carboxylate (III) (19.9 g) in 80 ml of tetrahydrofuran. The reaction mixture is then concentrated under reduced pressure. On cooling, the product precipitates in the form of crystals. Further amounts of product are obtained from the residue by crystallization from toluene: 5-methylisoxazole-4-carboxylic acid-(4-trifluoromethyl)-anilide having a melting point of 166.5° C.

5. 0.1 mol of 4-trifluoromethylaniline (II) (16.1 g) and 0.1 mol of benzyloxycarbonyl-5-methylisoxazole-4-carboxylate (III) (26.1 g) are dissolved in 150 ml of dioxan and refluxed for 90 minutes. The solvent is evaporated under reduced pressure. By crystallization from toluene, there is obtained from the residue 5-methylisoxazole-4-carboxylic acid-(trifluoromethyl)-anilide having a melting point of 166.5° C.

6. 0.1 mol of 4-trifluoromethylaniline (II) (16.1 g) and 0.1 mol (2,4-dichloro)phenyl-5-methylisoxazole-4-carboxylate (III) (27.2 g), dissolved in 150 ml of tetrahydrofuran, are refluxed for 2 hours. The mixture is evaporated to dryness under reduced pressure and, after recrystallization from toluene, there is obtained from the residue 5-methylisoxazole-4-carboxylic acid-(4-trifluoromethyl)anilide having a melting point of 166.5° C.

7. 0.1 mol of 4-trifluromethylaniline (II) (16.1 g) is refluxed for 2 hours with 0.1 mol of 5-methylisoxazole-4-carboxylic acid anhydride (III) (23.6 g) in 150 ml of acetonitrile. The mixture is heavily concentrated under reduced pressure and, after crystallization from toluene, there are obtained 5-methylisoxazole-4-carboxylic acid-(4-trifluoromethyl)-anilide having a melting point of 166.5° C.

Process variant (b)

Stage 1:

Acetoacetic acid-4-trifluromethylanilide of the formula IV

A mixture of 0.55 mole of diketene (46.3 g) and 30 ml of acetonitrile is added dropwise, at 75° C., to a solution of 0.5 mole of 4-trifluoromethylaniline (II) (30.6 g) in 150 ml of acetonitrile. The mixture is heated to boiling under reflux for 2.5 hours. When it has cooled to room temperature, the crystals which have precipitated are filtered off, washed with cold ethanol and dried. This gives 79.1 g (64.5% of theory) of crystalline acetoacetic acid-4-trifluoromethylanilide of the formula IV, melting point (after recrystallization from ethanol) 155° C.

The acetonitrile phase is evaporated to dryness under reduced pressure. The crystalline residue (42.1 g) is recrystallized from 80 ml of ethanol. This gives a further 24.1 g (19.7% of theory) of crystals. Melting point (after recrystallization from ethanol) 155° C.

Total yield: 84.2% of theory.

Stage 2:

2-Ethoxymethyleneacetoacetic acid 4-trifluoromethylanilide of the formula VI 0.75 mole of acetoacetic acid 4-trifluoromethylanilide (183.9 g) from stage 1 is boiled under reflux for 1.5 hours with 0.83 mole of orthoformic acid triethyl ester (V) (123 g) and 2.25 ml of acetic anhydride (229.7 g). After the mixture has cooled to room temperature, the crystals which have precipitated are filtered off and washed first with a small amount of acetic anhydride and then with petroleum ether. This gives 116.1 g (51.4% of theory) of crystalline 2-ethoxymethyleneacetoacetic acid 4-trifluoromethylanilide of the formula VI, melting point (after recrystallization from toluene) 124°–125° C.

The combined filtrates are concentrated under reduced pressure. The crystals of the crystal paste which thereupon remains are filtered off, washed first with a small amount of acetic anhydride and then with petroleum ether and dried. A further 56.1 g (24.8% of theory) of crystals are thus obtained. Melting point (after recrystallization from toluene) 124° to 125° C. Total yield: 76.2% of theory.

Stage 3:

5-Methylisoxazole-4-carboxylic acid 4-trifluoromethylanilide of the formula I 0.11 mole of hydroxylamine hydrochloride (7.65 g) is dissolved in 50 ml of water and an ice-cold solution of 0.11 mole of sodium hydroxide (4.4 g) in 10 ml of water is added. 0.1 mole of 2-ethoxymethyleneacetoacetic acid 4-trifluoromethylanilide of the formula VI (30.1 g) from stage 2, dissolved in 60 ml of ethanol, is then added dropwise to this hydroxylamine solution at 5° to 10° C. Thereafter the mixture is heated under reflux for 15 minutes. The crystals which have precipitated after cooling are filtered off, washed with water and dried.

19.6 g (72.6% of theory) of crystalline 5-methylisoxazole-4-carboxylic acid 4-trifluoromethyl-anilide of the formula I are thus obtained, melting point (after recrystallization from toluene) 166.5° C.

Pharmacological test and results

5-Methylisoxazole-4-carboxylic acid 4-trifluoromethyl-anilide of the formula I according to the invention [compound A] was tested in comparison with chemically closely related isoxazole derivatives known from United Kingdom Patent Specification No. 1,547,452, Table 2, No. 10, 11 and 12 namely 5-methylisoxazole-4-carboxylic acid 4-fluoroanilide [compound B], 5-methylixoazole-4-carboxylic acid 3-trifluoromethylanilide [compound C] and 5-methylisoxazole-4-carboxylic acid 3,5-bis-trifluoromethylanilide [compound D], and further with 5-methylisoxazole-4-carboxylic acid 2-trifluoromethylanilide [compound E] and with the known antiphlogistic agent phenylbutazone "compound F], in the animal models described below, for their antiphlogistic action, the effect on immunopathological processes, the ulcerogenic activity and the actue toxicity. The results of these investigations are summarized in Tables 1 and 2 below. According to these, the compound according to the invention is superior to the known compounds to a surprising degree.

1. Adjuvant arthritis, preventive experiment

The investigations were carried out by the method of Pearson (Arthrit.Rheum. 2, 440 (1959)). The experimental animals used were male rats of a Wistar-Lewis strain, having a body weight of between 130 and 200 g. The compounds to be compared were administered orally, daily from the 1st to the 17th day of the experiment. Animals of the control group were given the solvent only. For each dosage, and in the control group, a group of 8 animals was used. The criterion of the activity was the reduction in the paw volume increase compared to the untreated control group. The $ED_{50}$ values were determined graphically from the dose/effect curve.

2. Adjuvant arthritis, Perper modification (Proc.Soc..exp.Biol. Med. 137, 506 (1971))

The experimental animals and experimental methods were as under 1., but the animals were only treated from the 1st to the 12th day of the experiment; after a treatment-free interval of 9 days, the paw volume was determined on the 21st day. In this test, known non-steroid antiphlogistic agents are inactive, since they merely act symptomatically during the time of administration, and do not influence the immunopathological processes fundamental to adjuvant arthritis, so that the pattern of the illness develops fully up to the 21st day.

3. Allergic encephalomyelitis

This immunopathological illness pattern shows, like adjuvant arthritis, a number of parallels with certain illnesses of the rheumatic type (compare P. A. Miescher and H.-J. Müller-Eberhard, Textbook of Immunopathology, Grune and Stratton, New York p. 179 et seq. (1976)). Known non-steroid antiphlogistic agents are here at most very slightly active.

The investigations were carried out by the method of Levine (Arch.int.Pharmacodyn. 230, 309 (1977)). The experimental animals used were male rats of a Wistar-Lewis strain having a body weight of between 180 and 220 g. The encephalomyelitis was induced by injection of complete Freund adjuvant to which freshly withdrawn homogenized rat spinal marrow extract and Bordetella pertussis vaccine had been added. The compounds to be compared were administered orally once a day from the 1st to the 12th day. For each dose, and for the control group, a group of 10 animals was used. From the 7th day of the experiment, the paralysis symptoms were grouped together daily in one index with the mortality and the change of body weight.

The system employed was:
loss of 20 g of body weight in each case: 1 point
tail paralysis: 1 point
hindquarters paralysis: 3 points
paralysis of the entire body: 5 points
death: 5 points The assessment criterion was the percentage inhibition of the index compared to untreated control animals on the 11th day of the experiment. On conclusion of the experiment, blood was taken from the surviving animals to determine the erythrocyte count and leucocyte count as well as the hematocrit.

4. Acute ulcerogenic action

The investigations were carried out in groups of 10 male Sprague-Dawley rats having a body weight of 200-300 g. 48 hours before administration of the compounds to be compared, and up to the time of killing the animals, food was withheld, but there was free access to drinking water. The rats were killed 24 hours after oral administration, and the stomach was removed under running water and inspected for lesions of the mucous membrane. All macroscopically visible lesions were rated as ulcers. The proportion of animals with ulcers at each dose was determined, as was the $UD_{50}$ using the method of Litchfield and Wilcoxon (J.Pharmacol.exp.Ther. 96, 99 (1949)).

5. Sub-acute ulcerogenic action

The experimental animals and the experimental method were as under 4, with the following modification: the compounds to be compared were administered orally once daily for 4 days to normally fed rats and the animals were killed on the 5th day, after food had been withheld for 24 hours. According to Shriver, this method gives more informative results than a single administration, since medicamentous therapy of rheumatic patients also requires repeated treatment (Toxicology and Appl. Pharmacology 32, 73 (1975)).

6. Acute toxicity

The acute toxicity were determined by standard methods on NMRI mice and on rats of the Wister and Sprague-Dawley strains. 6 animals were used per dose. The $LD_{50}$ values were determined by the method of Litchfield and Wilcoxon.

TABLE 2

| Compound | Acute toxicity intraperitoneal administration to mice | Acute toxicity oral administration $LD_{50}$ (mg/kg) | species, strain | Therapeutic index $\dfrac{LD_{50}}{ED_{50}}$ |
| --- | --- | --- | --- | --- |
| A | 150-300 | 235 (157-332) | rats SPD | 100 |
| B | 200-400 | 620 (529-727) | rats Lewis | 41 |
| C | 100-250 | 740 (624-878) | mice NMRI | <15 |
| D | >500 | 2.530 (2.162-2.960) | mice NMRI | 50 |
| E | 300-6000 | | | |
| F | | 780 | rats | 21 |

The compound according to the invention, of the formula I, accordingly proves superior to the compounds according to German Offenlegungsschrift No. 2,524,959 in respect to the following pharmacological properties:

1. It exhibits an activity which is 6.5 times greater ($ED_{50}$, adjuvant arthritis, preventive) than that of 5-methylisoxazole-4-carboxylic acid 4-fluoroanilide (compound B).

2. Compared to known compounds from German Offenlegungsschrift No. 2,524,959, it exhibits a superior therapeutic range:

(a) in respect to the side effects on the gastric mucous membranes, especially after repeated administration: the therapeutic index ($UD_{50}/ED_{50}$; sub-acute) is 4.1 times greater than that of compound B;

(b) in respect to the oral toxicity: the therapeutic range ($LD_{50}/ED_{50}$) is 2.4 times greater than that of compound B.

3. It inhibits immunopathological processes in the Perper adjuvant arthritis test and in the allergic encephalomyelitis test in the therapeutic dosage range. The comparative compounds only achieve this to a much lesser degree; in particular, they cannot achieve 100% inhibition of the paralysis symptoms in allergic encephalomyelitis without gastro-intestinal bleeding, whereas this is possible with the formulation according to the invention.

The above pharmacological findings show that the compound according to the invention, of the formula I, differs advantageously in its pattern of action from the tested antiphlogistic agents, in particular in respect to the inhibition of immunopathological processes on animal models which are also relevant to human illnesses. This is probably equally true relative to other antiphlogistic agents hitherto employed in therapy. This fact

TABLE 1

| Compound | Adjuvant arthritis preventive (1) $ED_{50}$ mg/kg | Adjuvant arthritis Perper (2) $ED_{50}$ mg/kg | Allergic encephalomyelitis (3) dose mg/kg | Allergic encephalomyelitis (3) % inhibition | Ulcerogenic character (5) acute $UD_{50}$ (mg/kg) | Ulcerogenic character (5) sub-acute $UD_{50}$ (mg/kg) | Therapeutic index acute $\dfrac{UD_{50}}{ED_{50}}$ | Therapeutic index sub-acute $\dfrac{UD_{50}}{ED_{50}}$ |
| --- | --- | --- | --- | --- | --- | --- | --- | --- |
| A | 2.3 | 4.5 | 10 | 100 | 57 (40-82) | 77 (52-113) | 25 | 33 |
| B | 15.0 | 25.0 | 25 / 50 | 43 / anaemia | 250 (231-270) | 118 (97-144) | 17 | 8 |
| C | >50.0 | inactive up to 20.0 | 10 | 0 | of the order of the $LD_{50}$ ~600 | | <12 | |
| D | ~50.0 | >50.0 | | | 100 | | ~2 | |
| E | >50.0 | inactive up to 20.0 | 10 | 0 | 350 (177-693) | | <7 | |
| F | 37.0 | inactive up to 75 | 75 | 0 | 100 | | 3 | | opens up the possibility of tackling, by medication, rheumatic illnesses in man by more nearly treating the cause, instead of purely symptomatic treatment as with the antiphlogistic agents used hitherto.

In addition there is a possibility, in view of the histological and immunological parallels between allergic encephalomyelitis of test animals and human multiple sclerosis (compare, on this topic, T. L. Willmon, Ann.-N.Y.Acad. Sci. 122, 1–2 (1965)) of introducing a specific therapy, using the formulation according to the invention, even for this illness which has hitherto been difficult to tackle therapeutically.

What is claimed is:

1. 5-Methylisoxazole-4-carboxylic acid-4-trifluoromethyl-anilide of the formula

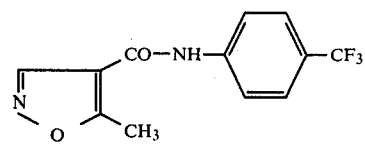

(i)

* * * * *